United States Patent
Ogawa et al.

(10) Patent No.: US 7,355,060 B2
(45) Date of Patent: Apr. 8, 2008

(54) METHOD FOR PRODUCING ORGANOSILANE

(75) Inventors: Tsuyoshi Ogawa, Yamaguchi (JP); Yoshihiro Muramatsu, Yamaguchi (JP); Mitsuya Ohashi, Yamaguchi (JP)

(73) Assignee: Central Glass Company, Limited, Ube-Shi (JP)

( * ) Notice: Subject to any disclaimer, the term of this patent is extended or adjusted under 35 U.S.C. 154(b) by 113 days.

(21) Appl. No.: 10/580,265

(22) PCT Filed: Nov. 9, 2004

(86) PCT No.: PCT/JP2004/016558

§ 371 (c)(1),
(2), (4) Date: May 25, 2006

(87) PCT Pub. No.: WO2005/051962

PCT Pub. Date: Jun. 9, 2005

(65) Prior Publication Data

US 2007/0149798 A1  Jun. 28, 2007

(30) Foreign Application Priority Data

Nov. 26, 2003 (JP) .............................. 2003-394883

(51) Int. Cl.
*C07F 7/08* (2006.01)
(52) U.S. Cl. ...................... 556/466; 556/478
(58) Field of Classification Search ...................... None
See application file for complete search history.

(56) References Cited

U.S. PATENT DOCUMENTS 4,595,777 A * 6/1986 Bakshi et al. ............... 556/478
4,999,447 A * 3/1991 Nelson ........................ 556/478

FOREIGN PATENT DOCUMENTS

JP 2004-331548 11/2004
WO WO 01/58908 A2 8/2001

OTHER PUBLICATIONS

Lukevics et al., "Ultrasound-Induced Heterogeneous Reduction of Halo, Alkoxy and Amino Derivatives of Group IVB Elements with Lithium Aluminium Hydride", Tetrahedron Letters, 1984, vol. 25, No. 13, pp. 1415-1416.
Jenn et al., "Synthesis of Tricyclopolyprenols via a Radical Addition and a Stereoselective Elimination", Part I: Methodology, Tetrahedron, 1998, vol. 54, No. 1-2, pp. 97-106.
Dehmlow et al., "Applicaations of Phase Transfer Catalysis, Part 48.1 a Re-evaluation of Tetra-alkylammonium Tetrahydridoaluminate and Phase Transfer Catalytic LiAlH4 Reductions", J. Chem. Research (S), 1,24, 1990.
Steward et al., "The Effect of Polar Substituents on the Alkali-catalyzed Hydrolysis of Triorganosilanes", J. Amer. Chem. Soc., 83, 1916 (1961).

* cited by examiner

*Primary Examiner*—Sikarl A. Witherspoon
(74) *Attorney, Agent, or Firm*—Crowell & Moring LLP

(57) ABSTRACT

By reducing an organosilane represented by the formula (1), $$SiX_nR_{4-n} \quad (1)$$

(wherein X represents a halogen or alkoxide, n represents an integer of 1-3, and R represents an alkyl group or aryl group), there is produced a corresponding organosilane represented by the formula (2), $$SiH_nR_{4-n} \quad (2)$$

(wherein n represents an integer of 1-3, and R represents an alkyl group or aryl group). In this production method, an aromatic hydrocarbon series organic solvent is used as a reaction solvent, and aluminum lithium hydride is used as a hydrogenating agent.

4 Claims, No Drawings

METHOD FOR PRODUCING ORGANOSILANE

TECHNICAL FIELD

The present invention relates to a method for producing organosilanes, which are useful for film-forming raw materials in semiconductor production or for organic syntheses.

BACKGROUND OF THE INVENTION

Organosilanes, particularly methylsilane ($CH_3SiH_3$) and trimethylsilane (($CH_3$)$_3SiH$), are raw material gases that are useful as CVD film-forming materials in semiconductor device production. Particularly in recent years, they attract attention as raw material gases of low-dielectric-constant insulating films. In methods for producing organosilanes, it is general to use a method in which a reducing agent, such as aluminum lithium hydride ($LiAlH_4$), is used in a polar organic solvent, such as diethyl ether ($C_2H_5OC_2H_5$), dimethoxyethane (DME), diglyme (DGM) or tetrahydrofuran (THF). It is superior in product purity and yield, too. Hitherto, it has been considered that the reduction reaction by $LiAlH_4$ occurs only in a polar solvent and that the reaction does not occur in a non-polar hydrocarbon series solvent such as hexane and heptane. There have been no publications or the like having disclosures other than reaction examples using polar solvents as reaction solvents of organosilanes. Although a $LiAlH_4$ reduction of cyclohexanone has been tried in toluene solvent that is one of aromatic hydrocarbon series organic solvents used in the present invention, cyclohexanol that should be obtained by the reduction has not been found (Non-patent Publication 1). It is generally considered that $AlH_4^-$ ion is produced in an organic solvent by dissociation in $LiAlH_4$ reduction, and this acts on the reaction substance to generate the reaction. Therefore, it is considered that the reaction proceeds only in a polar solvent that can dissolve $LiAlH_4$ and that the reaction does not occur since it is not possible to dissolve $LiAlH_4$ in a solvent that has little polarity, such as toluene.

As an organosilane synthesis example using a polar solvent, there is described a method for synthesizing ($CH_3$)$_3SiH$ with a yield of 85% by reacting trimethylchlorosilane (($CH_3$)$_3SiCl$) with $LiAlH_4$ under reflux at a temperature of 86° C. using DME solvent (Non-patent Publication 2). Furthermore, there is described a method for synthesizing ($CH_3$)$_3SiH$ with a yield of 91% by reacting ethoxytrimethylsilane (($CH_3$)$_3SiOC_2H_5$) with $LiAlH_4$ at a temperature of 50-70° C. using DGM solvent (Patent Publication 1).

However, in these methods using polar solvents, organosilanes that are in salvation remain in the residual liquids after the termination of the reactions. The difficulty in their recovery caused lowering of yield. In the case of treating the reaction residual liquid, it was difficult to recover the solvent by the treatment with water, since all of the solvents other than diethyl ether are water-soluble. Even in the case of using a method of recovering the solvent from the reaction residual liquid through evaporation, a separation from the residue was difficult due to high polarity of the solvent, and the solvent recovery use was extremely difficult.

Patent Publication: WO 01/58908

Non-patent Publication 1: J. Chem. Res. (S), 1, 24 (1990)

Non-patent Publication 2: J. Amer. Chem. Soc., 83, 1916 (1961)

SUMMARY OF THE INVENTION

It is an object of the present invention to provide a method for producing an organosilane of high purity with high yield and with good productivity, while solving a problem possessed by conventional polar solvents.

According to the present invention, there is provided a method for producing an organosilane, in which an organosilane represented by the formula (1), $$SiX_nR_{4-n} \qquad (1)$$

(wherein X represents a halogen or alkoxide, n represents an integer of 1-3, and R represents an alkyl group or aryl group) is reduced, thereby producing a corresponding organosilane represented by the formula (2), $$SiH_nR_{4-n} \qquad (2)$$

(wherein n represents an integer of 1-3, and R represents an alkyl group or aryl group), which is characterized in that an aromatic hydrocarbon series organic solvent is used as a reaction solvent and that aluminum lithium hydride is used as a hydrogenating agent.

DETAILED DESCRIPTION

According to the method of the present invention, it is possible to easily recover the solvent used in the reaction and to produce an organosilane of high purity with high yield and good productivity.

According to the present invention, there is used a slightly polar solvent that is insoluble in water. Therefore, it is possible to easily recover the solvent by subjecting the reaction residual liquid to washing with water and to liquid separation. Since it has almost no polarity, it is possible to recover almost the total amount of an organosilane produced by the reaction, and it can be produced with very high yield. Furthermore, aromatic hydrocarbons are generally high in boiling point. Therefore, the amount of the solvent accompanied with the produced organosilane is small, and it is possible to relatively easily achieve ultra high purity that is required in case that it is used as a semiconductor film-forming material gas.

According to the present invention, it is possible to produce an organosilane by reacting an organohalosilane or the like, which is a raw material, with $LiAlH_4$ in an aromatic hydrocarbon series solvent that is a slightly polar solvent under a condition of 40-120° C. In this case, it was found to be a self-catalyst reaction in which $LiAlCl_4$ produced by by-production becomes a catalyst. It was found that the reaction rate of the initial stage increases remarkably by adding $LiAlCl_4$ particularly at the start of the reaction and thereby an organosilane can safely and stably be produced.

In the following, the present invention is exemplarily described in detail. An organohalosilane or the like that is used as the raw material in the present invention is one represented by the formula (1), $$SiX_nR_{4-n} \qquad (1)$$

wherein X represents a halogen or alkoxide, n represents an integer of 1-3, and R represents an alkyl group or aryl group. Examples of R are alkyl groups such as methyl group, ethyl group, propyl group and isopropyl group, and aryl groups. In case that a plurality of R exist, these may be the same or different from each other. As X, it is possible to use fluoro group, chloro group, bromo group, iodo group, methoxy group, ethoxy group and the like. In general, one having a chloro group(s), which is easily available and low in price, is preferably usable.

It suffices that the solvent to be used is a hydrocarbon series solvent containing an aromatic ring, but it must be one that can dissociate and dissolve $AlCl_4^-$ ions. Specifically, it is possible to cite benzene, toluene, xylene, ethylbenzene, butylbenzene, and anisole.

In order to make the reaction proceed smoothly, the addition of catalyst is essential in the present invention. That is, in case that the catalyst does not exist, the reducing power of $LiAlH_4$ is low and the reaction is extremely slow in an aromatic hydrocarbon series solvent that is low in polarity. The catalyst is not particularly limited, as long as it is a substance that releases $AlCl_4^-$ ions. Specifically, $LiAlCl_4$, $NaAlCl_4$, $KAlCl_4$ and the like are cited. $LiAlCl_4$ is particularly preferable. In case that a chloride is used as the organohalosilane or the like of the raw material, it becomes a self-catalyst reaction, since $LiAlCl_4$ is produced as a by-product as the reaction proceeds. Therefore, if the reaction is conducted with no catalyst, the reaction rate is slow at the initial stage of the reaction, and the reaction rate increases remarkably as the reaction proceeds. As a result, in case that the introduction rate of the chloride of the raw material is high, it is extremely dangerous since the reaction often proceeds at once and crashes. $AlCl_3$ is famous as a reaction catalyst of $LiAlH_4$. However, it hardly acts as a catalyst in the present invention.

As the catalyst, $LiAlCl_4$ itself may be used, and a mixture of LiCl and $AlCl_3$ (1:1), which is easily available, may also be used. In case that a chloride is used as the raw material, it is also possible to reuse a part of $LiAlCl_4$ that has been produced in the reaction residual liquid. It is preferable to add the catalyst to be greater than solubility in the solvent. For example, in case that toluene is used as the solvent, it is added preferably in 0.02 g/ml or greater.

In the present invention, the reaction is conducted at a reaction temperature of 40° C.-120° C., preferably 60-100° C. If it is less than 40° C., the reduction capacity is low, and the reaction becomes very slow. If it exceeds 120° C., danger is caused due to the occurrence of decomposition reaction of $LiAlH_4$.

After the termination of the reaction, it is possible to recover the organosilane that is dissolved in the solvent by heating or depressurizing the reactor. The dissolved organosilane is not subjected to solvation. Therefore, it is possible to recover the total amount of the dissolved organosilane. In the case of using a chloride as the raw material, the reaction residual liquid is immediately separated into two layers of the solvent layer and the residue layer of $LiAlCl_4$. Therefore, it can easily be separated into the residue and the solvent by liquid separation. $LiAlCl_4$ is dissolved in the recovered solvent. By using this again in the reaction, it becomes unnecessary to newly add the catalyst.

It is possible to easily recover the pure solvent by conducting washing with hydrochloric acid or washing with water and then the liquid separation in the treatment of the residual liquid.

In the following, the present invention is specifically described by examples, but the present invention is not limited to the following examples.

EXAMPLE 1

A 500 ml glass flask equipped with a reflux condenser was replaced with helium gas. The flask was charged with $LiAlH_4$ of 1.16 g (0.031 mol) and toluene of 30 ml, followed by stirring, increasing the temperature to 80° C., and then adding $(CH_3)_3SiCl$ of 14ml (0.110 mol) in a dropwise manner by 10 min. Gas generation did almost not occur immediately after the dropping, but gas generation occurred gradually with the dropping. At a point when ⅓ was dropped, an abrupt bubbling was observed. The generated gas was passed through the reflux condenser, and then the total amount was collected in a trap chilled by liquid nitrogen, followed by measuring the weight. The collected gas was identified and quantified by a gas chromatograph and a gas chromatograph-mass spectrometer. The obtained gas was $(CH_3)_3SiH$. Purity was 96.9 vol %, and yield was 92.5%.

EXAMPLE 2

The reaction was conducted by the same method as that of Example 1, except in that the flask was charged with $LiAlCl_4$ of 0.6 g (0.004 mol) as the catalyst together with $LiAlH_4$. Gas generation was found from immediately after the dropping of $(CH_3)_3SiCl$. An abrupt bubbling was not found, and the reaction proceeded mildly. The collected gas was $(CH_3)_3SiH$. Purity was 98.1 vol %, and yield was 92.7%.

EXAMPLE 3

The reaction was conducted by the same method as that of Example 1, except in that the flask was charged with $AlCl_3$ of 0.5 g (0.004 mol) and LiCl of 0.13 g (0.003 mol) as the catalyst together with $LiAlH_4$. Gas generation was found from immediately after the dropping of $(CH_3)_3SiCl$. An abrupt bubbling was not found, and the reaction proceeded mildly. The collected gas was $(CH_3)_3SiH$. Purity was 97.8 vol %, and yield was 94.4%.

EXAMPLE 4

The reaction was conducted by the same method as that of Example 1, except in that 30 ml of the liquid of the solvent layer of the reaction residual liquid were used in place of toluene. Gas generation was found from immediately after the dropping of $(CH_3)_3SiCl$. An abrupt bubbling was not found, and the reaction proceeded mildly. The collected gas was $(CH_3)_3SiH$. Purity was 92.4 vol %, and yield was 94.3%.

EXAMPLE 5

The reaction was conducted by the same method as that of Example 3, except in that 30 ml of xylene were used in place of toluene. Gas generation was found from immediately after the dropping of $(CH_3)_3SiCl$. An abrupt bubbling was not found, and the reaction proceeded mildly. The collected gas was $(CH_3)_3SiH$. Purity was 96.3 vol %, and yield was 95.4%.

EXAMPLE 6

The reaction was conducted by the same method as that of Example 3, except in that 4 ml (0.037 mol) of $CH_3SiCl_3$ were added in a dropwise manner in place of $(CH_3)_3SiCl$. Gas generation was found from immediately after the dropping of $CH_3SiCl_3$. An abrupt bubbling was not found, and the reaction proceeded mildly. The collected gas was $CH_3SiH_3$. Purity was 96.8 vol %, and yield was 93.1%.

EXAMPLE 7

The reaction was conducted by the same method as that of Example 3, except in that the reaction temperature was 40° C. Gas generation was found from immediately after the dropping of $(CH_3)_3SiCl$, but the amount of the gas generated was small. Even after the termination of the dropping, the gas generation continued. The reaction terminated 6 hr later. The collected gas was $(CH_3)_3SiH$. Purity was 94.8 vol %, and yield was 81.3%.

EXAMPLE 8

The reaction was conducted by the same method as that of Example 3, except in that the reaction temperature was 120° C. Gas generation was found from immediately after the dropping of $(CH_3)_3SiCl$. An abrupt bubbling was not found, and the reaction proceeded mildly. The collected gas was $(CH_3)_3SiH$. Purity was 93.5 vol %, and yield was 78.1%.

EXAMPLE 9

The reaction was conducted by the same method as that of Example 3, except in that the initial temperature was 25° C. Gas generation did almost not occur until the termination of the dropping of $(CH_3)_3SiCl$. When the temperature was increased to 80° C. with stirring, an abrupt bubbling was observed 5 min later (80° C.). Therefore, the generated gas was collected in a trap. The collected gas was $(CH_3)_3SiH$. Purity was 93.5 vol %, and yield was 91.1%.

EXAMPLE 10

A 1.5L stainless steel reactor equipped with a reflux condenser was replaced with helium gas. The reactor was charged with $LiAlH_4$ of 24.85 g (0.655 mol), $AlCl_3$ of 5.02 g (0.038 mol), LiCl of 1.60 g (0.038 mol) and toluene of 321 ml, followed by stirring, increasing the temperature to 80° C., and then adding $(CH_3)_3SiCl$ of 300 ml (2.364 mol) in a dropwise manner by 3 hr. Gas generation was found from immediately after the dropping. An abrupt bubbling was not found, and the reaction proceeded mildly. The collected gas was $(CH_3)_3SiH$. Purity was 98.0 vol %, and yield was 96.6%. 300 ml of 1% hydrochloric acid were added to the reaction residual liquid after the reaction, and the aqueous layer was taken out from the lower layer. The organic layer of the upper layer was obtained 318 ml. It was toluene having a purity not lower than 99%.

COMPARATIVE EXAMPLE

The reaction was conducted by the same method as that of Example 1, except in that 30 ml of tetrahydrofuran (THF) were used as the solvent in place of toluene and that the reaction temperature was room temperature. Gas generation was found from immediately after the dropping of $(CH_3)_3SiCl$. An abrupt bubbling was not found, and the reaction proceeded mildly. The collected gas was $(CH_3)_3SiH$. Purity was 76.2 vol %, and yield was 71.4%.

The invention claimed is:

1. A method for producing an organosilane, in which an organosilane represented by the formula (1), $$SiX_nR_{4-n} \qquad (1)$$

(wherein X represents a halogen or alkoxide, n represents an integer of 1-3, and R represents an alkyl group or aryl group) is reduced, thereby producing a corresponding organosilane represented by the formula (2), $$SiH_nR_{4-n} \qquad (2)$$

(wherein n represents an integer of 1-3, and R represents an alkyl group or aryl group),
  which is characterized in that an aromatic hydrocarbon series organic solvent is used as a reaction solvent and that aluminum lithium hydride is used as a hydrogenating agent.

2. A method for producing an organosilane according to claim 1, which is characterized in that the reaction temperature is 40-120° C.

3. A method for producing an organosilane according to claim 1, which is characterized in that a substance that releases $AlCl_4^-$ ions in the organic solvent is used as a catalyst.

4. A method for producing an organosilane according to claim 3, which is characterized in that the catalyst is $LiAlCl_4$.

* * * * *